Figure 1:
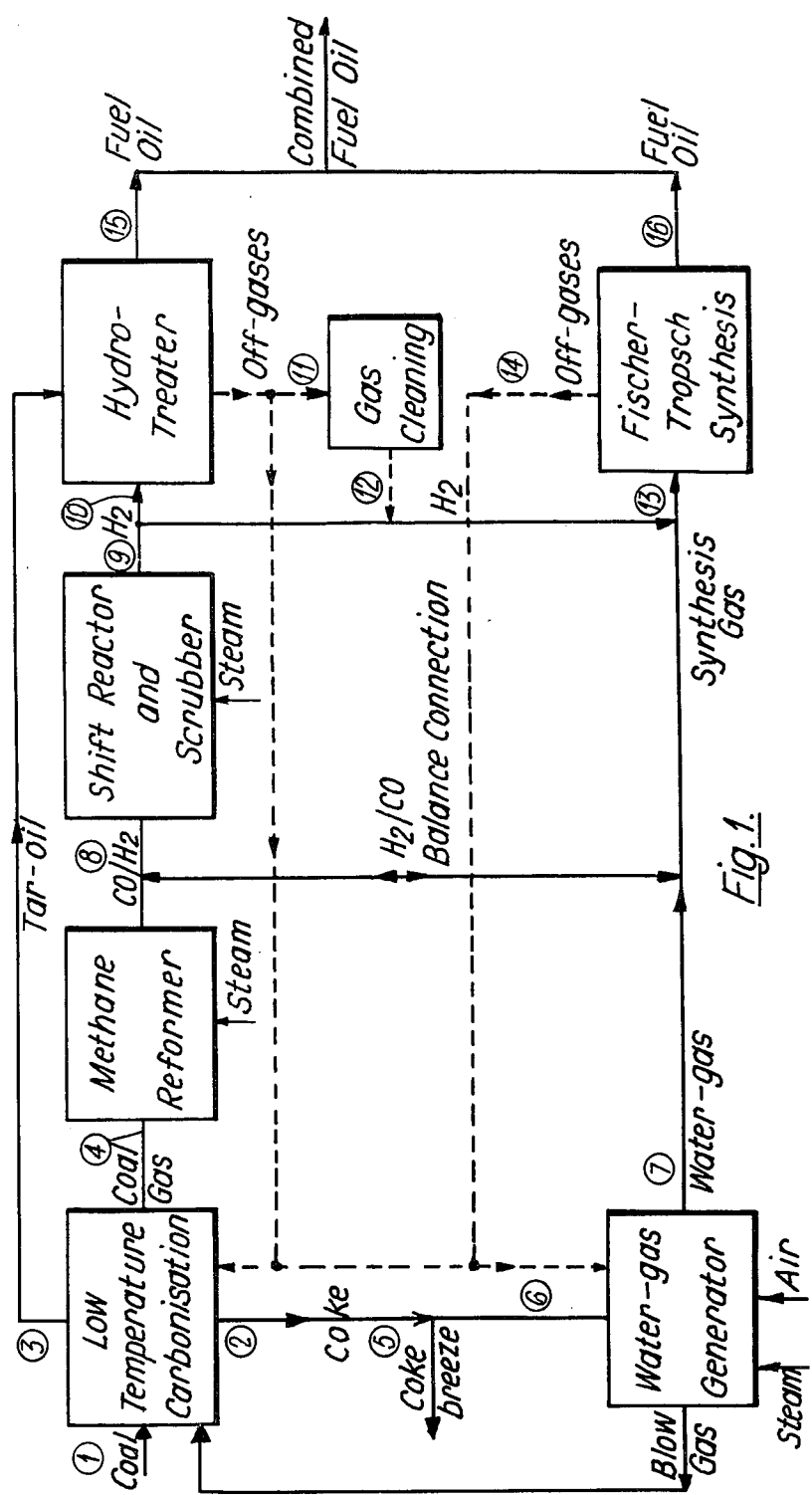

United States Patent [19]

Hollaway

[11] 4,076,612
[45] Feb. 28, 1978

[54] PROCESS FOR OBTAINING LIQUID FUEL-OIL AND/OR GASEOUS HYDROCARBONS FROM SOLID CARBONACEOUS FEED STOCKS

[75] Inventor: John William Hollaway, Eiffel Flats, Rhodesia

[73] Assignee: Rio Tinto (Rhodesia) Limited, Salisbury, Rhodesia

[21] Appl. No.: 530,557

[22] Filed: Dec. 9, 1974

[30] Foreign Application Priority Data

Dec. 7, 1973 Rhodesia .................................... 475
May 22, 1974 Rhodesia .................................... 201

[51] Int. Cl.² ........................ C10G 1/02; C07C 27/00
[52] U.S. Cl. ................................ 208/8; 260/449 R; 48/197 R
[58] Field of Search ............... 208/8, 10; 48/197 R, 48/210; 252/373; 423/655, 650; 260/449 R

[56] References Cited

U.S. PATENT DOCUMENTS

| 2,605,174 | 7/1952 | Krejci ............................ 252/373 |
| 2,634,286 | 4/1953 | Elliot et al. ...................... 208/8 |
| 2,697,718 | 12/1954 | Gohr et al. ...................... 208/8 |
| 2,719,130 | 9/1955 | Stewart ......................... 48/197 R |
| 2,892,685 | 6/1959 | Paull ............................ 423/655 |
| 3,030,297 | 4/1962 | Schroeder ........................ 208/8 |
| 3,231,486 | 1/1966 | Perry et al. ....................... 208/8 |
| 3,503,866 | 3/1970 | Skripek et al. ................. 48/197 R |
| 3,503,867 | 3/1970 | Ludlam et al. ................. 48/197 R |
| 3,552,924 | 1/1971 | Hepp ............................ 252/373 |

OTHER PUBLICATIONS

Lowry, H. H., Chemistry of Coal Utilization, vol. II, John Wiley & Sons, New York, 1945, pp. 1804, 1806.

*Primary Examiner*—Delbert E. Gantz
*Assistant Examiner*—James W. Hellwege
*Attorney, Agent, or Firm*—Young & Thompson

[57] ABSTRACT

A process for forming a fuel-oil from coal. The coal is treated in a low temperature carbonisation retort to give coke, coal-gas and tar-oil. The coke is converted to water-gas which is then synthesised in a Fischer-Tropsch synthesiser to form fuel-oil. The tar-oil is hydrogenated in a hydro-treater by hydrogen produced from the coal-gas. Hydrogen is produced from coal-gas either in a thermal cracking chamber or by reforming the methane content to hydrogen and passing the resultant hydrogen/carbon monoxide mixture through a water-gas shift reactor and a carbon dioxide scrubber.

10 Claims, 2 Drawing Figures

Fig. 1.

PROCESS FOR OBTAINING LIQUID FUEL-OIL AND/OR GASEOUS HYDROCARBONS FROM SOLID CARBONACEOUS FEED STOCKS

This invention relates to a process for obtaining liquid fuel-oil and/or gaseous hydrocarbons from solid carbonaceous feed stocks. More particularly, the invention is concerned with a process of obtaining a high yield of hydrocarbon fuel-oil from coal. In this specification by the term "fuel-oil" is meant a synthetic oil suitable for use as a refinery feed stock.

There are a member of known processes for producing oil from coal, but all of these give poor recoveries by weight of liquid products relative to the weight of coal used.

One known process involves direct hydrogenation of a mixture of coal together with heavy oil produced from the process. The hydrogenation is carried out over a catalyst at high pressures (usually greater than 200 bars) and at temperatures of about 400° C. The oil formed can be further hydrogenated in its vapour phase. This type of process was used at the Leuna Works of IG Farben Industrie AG, during the period 1935 – 1945. Other examples of this process are the H-Coal Process in America which was used on pilot scale only and at the Imperial Chemical Industries Plant at Billingham in the United Kingdom up to 1940.

A solvent extraction method has also been utilised where finely crushed coal is subjected to a coal solvent such as Tetralin or Toluene. Much of the "coaly matter" comes into solution and is then hydrogenated to lighter oils and petrol. The carbonaceous residue could be used as a fuel. This process has not to the knowledge of the applicant been used commercially, but has been used in America and South Africa on a pilot scale only.

A Fischer-Tropsch synthesis process has also been utilised where the coal is gasified with steam and oxygen to give nitrogen free "water-gas" ($CO + H_2$ mixture). This is then synthesised into hydrocarbon and alcohols by the Fischer-Tropsch reaction. This process was used in Germany until 1945 at the Bohlen Works and a later adaption is utilised in South Africa by Sasol.

Another known method is by carbonising the coal at temperatures of over 1000° C to produce metallurgical coke and heavy viscous coal-tar as a by-product, which is then hydrogenated to petrol and other fuel-oil fractions.

Alternatively, the coal was coked at temperatures between 500° and 1000° C with the result that more tar and less gas was produced than the high temperature of carbonisation described above. A large number of these low temperature carbonisation processes have been tried and no standard process has yet been evolved. The tar is hydrogenated as described above for the high temperature carbonisation with the exception that the hydrogenation conditions are moderate compared to high temperature hydrogenation. This process was utilised, for example, at Politz-Stettin in Germany until 1945 and at Imperial Chemical Industries Works at Billingham in the United Kingdom until 1958.

The disadvantages of the above processes may be summarised as follows. Direct hydrogenation; this requires an external hydrogen source and utilises extreme pressures and temperatures which result in a high capital cost of equipment. Solvent extraction; this also requires an external hydrogen source. Fischer-Tropsch synthesis; this tends to be a very inefficient process in which about 5 tons of coal yield 1 ton of liquid products. The capital cost of equipment is fairly high and it is necessary that there should be a subsidiary market for fuel gases, alcohol, etc., for the plant to run profitably. High temperature and low temperature carbonisation; this gives a limited yield, about 100 liters per ton of coal.

The process of the present invention is based on an integration of the Fischer-Tropsch synthesis process and the carbonisation process. This integrated process obviates the necessity for an external hydrogen source by fully utilising the hydrogen present in the coal-gas and gives a better yield than the Fischer-Tropsch synthesis process or carbonisation process by themselves.

A process for obtaining hydrocarbon fuel-oil from coal according to the invention includes the steps of treating the coal to form a tar-oil, coal-gas and coke, producing a gas mixture containing hydrogen and carbon monoxide from the coke, synthesising the gas mixture into fuel-oil and hydrogenating the tar-oil to produce further fuel-oil.

Preferably, the coal-gas is treated to form hydrogen, part of which is added to the gas mixture to enhance the yield of fuel while the remaining part serves to hydrogenate the tar-oil. The coal-gas may be treated by thermal cracking or by reforming it with steam in the presence of a catalyst to give a hydrogen/carbon monoxide mixture which is fed to a water-gas shift reactor to produce a hydrogen/carbon dioxide mixture, the carbon dioxide being removed by a conventional scrubber.

Figure 2:
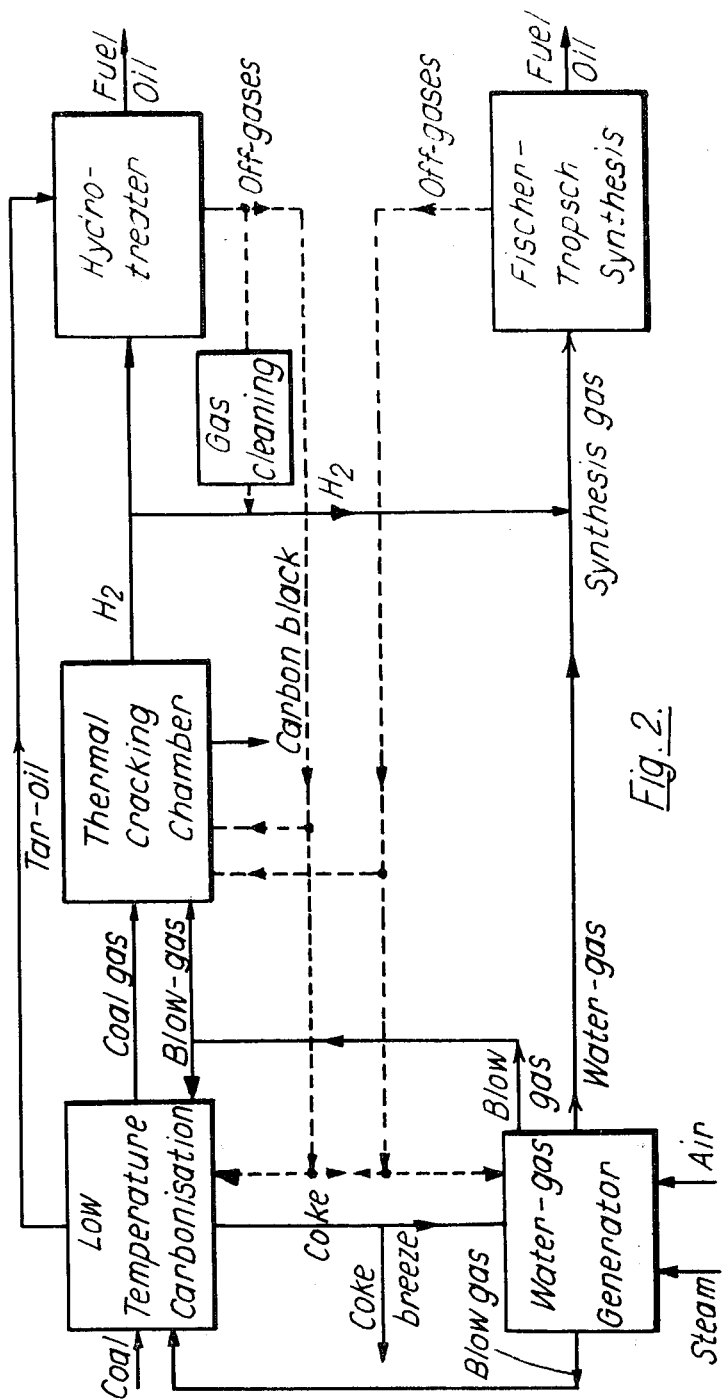

The invention will now be described by way of example with reference to the accompanying drawings, in which:

FIG. 1 is a flow diagram of a process according to one embodiment of the invention; and FIG. 2 is a flow diagram of a process according to an alternative embodiment of the invention.

The accompanying Table is a Mass Balance Schedule of the process of FIG. 1. In FIG. 1 the numerals are a cross-reference to the Mass Balance Schedule.

In FIG. 1 the initial step is to utilise a low temperature carbonisation technique to treat the coal which produces a lump coke, a high quality gas and a low temperature tar-oil.

By limiting the amount of moisture present in the retort during carbonisation it has been shown that dramatic increases in the quantity of oils produced are possible. Thus a yield of tar-oil to the extent of approximately 20% by weight of ash free coal charged can be predicted with a high degree of confidence.

The coke (char) produced by the low temperature carbonisation system is then treated in a water-gas generator. The water-gas produced is a mixture of hydrogen and carbon monoxide which is then fed to a vessel in which Fischer-Tropsch hydrocarbon synthesis takes place. However, there is sufficient hydrogen present. The gas to be synthesised should contain twice the volume of hydrogen for each volume of carbon monoxide and in water-gas this ratio is about 1.25:1. Thus more hydrogen must be manufactured. This is achieved in part by utilising the coal-gas from the carbonisation process. The firing of the carbonisation retorts normally undertaken with this gas can be replaced by the heat available in the blow-gas from the water-gas generator.

However, the coal-gas has a high methane content along with ethane, etc, and this is reformed with steam over a catalyst to give a hydrogen/carbon monoxide mixture. This mixture passes to a water-gas shift reactor wherein the carbon monoxide is changed to carbon dioxide and extra hydrogen is generated. The methane reformer and the shift reactor are both conventional equipment, the methane reforming usually being accomplished by the addition of steam over a nickel catalyst at a temperature of 550° C, the shift reaction also being accomplished by the addition of steam over a catalyst at 500° C. The carbon dioxide is scrubbed out leaving a gas containing about 95% hydrogen.

The hydrogen rich gas manufactured as described above is split into two parts. One part is used to adjust the ratios in the water-gas prior to the conventional Fischer-Tropsch gas purification and synthesis step. The remaining part is introduced into a hydro-treater where the tar-oils from the low temperature carbonisation process undergo a mild hydrogenation to form a fuel-oil suitable as a refinery feed stock.

The hydrogen deficiency of the water-gas may be adjusted by a balance connection between the lines containing the output from the water-gas generator and the output from the methane reforming section. This balance connection may be used as an alternative to or in addition to the hydrogen added from the outlet from the shift reactor section. The balance connection may also be utilised to direct water-gas to the shift reactor. The direction in which the gas flows through this connection depends upon the type of coal being treated. Should the type of coal being treated in the carboniser yield a limited amount of coal-gas, with the result that there is an insufficient supply of hydrogen produced by the methane reformer and shift reactor to supply the hydro-treater and the Fischer-Tropsch synthesis section then a portion of the water-gas can be passed through the shift reactor and scrubber to make up the deficiency. Conversely, if a coal which produces a large quantity of coal-gas is being used then the excess gas produced from the methane reforming section may be added to the water-gas. The balance connection enables maximum use of the hydrogen contained in the coal and consequently minimises carbon loss due to the water-gas shift reaction occurring at the water-gas generator and in the shift reactor, thus $$CO + H_2O \rightarrow CO_2 + H_2$$

This results in increased efficiency in terms of oil yield from the coal treated. From the Mass Balance Sheet it can be seen that 120 kg of coal containing 11.7% of ash (100 kg dry ash free coal) yields 38.24 kg of liquid products, i.e. 3.14 tons of coal per ton of liquid products. At 25% ash this increases to 3.5 tons of coal per ton of liquid products.

Despite the high yield of oils it appears that the plant will be self sufficient in power and steam.

If reference is now made to FIG. 2 it can be seen that instead of reforming the coal-gas with steam in the presence of a catalyst to give the hydrogen/carbon monoxide mixture and then passing this mixture into a shift reactor to convert the carbon monoxide to carbon dioxide to form more hydrogen, the hydrogen is formed directly by the thermal cracking of the methane content of the coal-gas according to the formula:

$$CH_4 \rightarrow C + 2H_2$$

The thermal cracking process is normally carried out in a refractory cracking chamber which is alternately heated to red heat and then the methane rich gas is blown through. This gives a yield of solid carbon in the form of carbon-black plus hydrogen. The process is highly endothermic but it is possible to use the blow-gas from the water-gas generator or off-gases from the hydro-treater and/or off-gases from the Fischer-Tropsch reactor to supply the heat to the thermal cracking chamber. Part of the blow-gas may also be used to fire the low temperature carbonisation retort or the retort may be fired by the off-gases. The carbon-black formed as a by-product has several commercial uses.

In FIGS. 1 and 2 there is shown by means of a broken chain various methods by which the off-gases from the hydro-treater and the Fischer-Tropsch synthesis section may be recirculated to the system. This is highly desirable as the off-gases comprise gaseous hydrocarbon and hydrogen which has been gained only by the expense of heat input into the system. By recirculation of the off-gases increased yields are obtained.

There are several points to which the off-gases may be recirculated and the process chosen will depend on the circumstances.

For example, the off-gases from the hydro-treater, being mainly hydrogen, may be recirculated to the hydrogen stream passing to the Fischer-Tropsch synthesis section.

The off-gases from the Fischer-Tropsch synthesis section and/or the hydro-treater may be recirculated to the low temperature carboniser. This modification enhances the efficiency of the carboniser and this effect is thought to be due to the high heat conductive transfer co-efficient of hydrogen gas. Alternatively, the Fischer-Tropsch off-gases and/or the hydro-treater off-gases may be recirculated to the water-gas generator which results in a higher hydrogen content in the gas due to the cracking of the hydrocarbons present in these gases.

With reference to FIG. 2 only, the Fischer-Tropsch off-gases and/or the hydro-treater off-gases may be recirculated to the thermal cracking chamber where the hydrocarbons present are converted to hydrogen and carbon-black. This results in a greater yield of hydrogen.

I claim:

1. In a process of obtaining hydrocarbon fuel-oils from coal, comprising the steps of:
   (a) treating the coal by low temperature carbonization at a temperature of 500° – 1000° C to form tar-oil, coal-gas and coke;
   (b) passing said coke formed at low temperature direct to a water-gas reaction and producing a gas mixture containing hydrogen and carbon monoxide from the coke by said water-gas reaction;
   (c) synthesizing the gas mixture into fuel-oil by a Fischer-Tropsch type synthesis;
   (d) treating the coal-gas to form hydrogen and carbon monoxide;
   (e) generating a hydrogen stream from the gas produced in step (d) by passing the hydrogen and carbon monoxide through a a water-gas shift reactor and a carbon dioxide scrubber.
   (f) adding part of the gas from step (e) to step (c); and
   (g) hydrogenating the tar-oil with the remainder of the gas from step (e);
   the improvement comprising
   (h) adding part of the gas produced in one of steps (b) and (d) to the gas produced in the order of steps (b) and (d), the addition being in the direction (b) to (e) when the amount of hydrogen that would otherwise arrive in (c) is less than twice the amount of carbon monoxide and in the direction (d) to (c)

when the amount of hydrogen that would otherwise arrive in (c) is more than twice the amount of carbon monoxide, thereby to make maximum use of the hydrogen contained in the coal and consequently minimize carbon loss due to the water-gas shift reaction occurring in (b) and (e), and to maintain a 2:1 ratio of hydrogen to carbon monoxide in (c).

2. A process according to claim 1 wherein the coal-gas is treated by reforming it with steam in the presence of a catalyst to give a hydrogen/carbon monoxide mixture.

3. A process according to claim 1 wherein the tar-oil is hydrogenated in a hydro-treater at elevated temperature and pressure in the presence of a catalyst.

4. A process as claimed in claim 1 wherein the off-gases from the gas mixture synthesising step are recirculated to the coal treatment step.

5. A process according to claim 1 wherein the off-gases from the tar-oil hydrogenating step are recirculated to the coal treatment step.

6. A process according to claim 1 wherein the off-gases from the gas mixture synthesising step and the off-gases from the tar-oil hydrogenating step are recirculated to the coal treatment step.

7. A process according to claim 1 wherein the off-gases from the gas mixture synthesising step are recirculated to the gas mixture producing step.

8. A process according to claim 1 wherein the off-gases from the tar-oil hydrogenating step are recirculated to the gas mixture producing step.

9. A process according to claim 1 wherein the off-gases from the gas mixture synthesising step and the off-gases from the tar-oil hydrogenating step are recirculated to the gas mixture producing step.

10. A process according to claim 1 wherein the off-gases from the tar-oil hydrogenating step are recirculated to the gas mixture synthesising step.

* * * * *